US009068939B2

(12) United States Patent
Dasgupta et al.

(10) Patent No.: US 9,068,939 B2
(45) Date of Patent: Jun. 30, 2015

(54) NANO SENSING OF TEMPERATURE USING EQUAL INTENSITY DOUBLE PLASMON RESONANCE (EIDPR)

(75) Inventors: Anjan Kr. Dasgupta, Kolkata (IN); Sarita Roy, West Bengal (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 165 days.

(21) Appl. No.: 13/503,815

(22) PCT Filed: Jun. 21, 2011

(86) PCT No.: PCT/IB2011/001392
§ 371 (c)(1),
(2), (4) Date: Apr. 24, 2012

(87) PCT Pub. No.: WO2012/127272
PCT Pub. Date: Sep. 27, 2012

(65) Prior Publication Data
US 2013/0027706 A1    Jan. 31, 2013

(30) Foreign Application Priority Data
Mar. 21, 2011  (IN) .............................. 375/KOL/2011

(51) Int. Cl.
*G01N 21/00*  (2006.01)
*G01N 21/552*  (2014.01)
*G01N 33/553*  (2006.01)
*B82Y 15/00*  (2011.01)

(52) U.S. Cl.
CPC ............ *G01N 21/554* (2013.01); *G01N 33/553* (2013.01); *B82Y 15/00* (2013.01)

(58) Field of Classification Search
CPC ............ C12Q 1/6837; C12Q 2565/628; C12Q 2563/155; G01N 21/554; G01N 21/553; G01N 33/553; G01N 21/658; G01N 2021/258
See application file for complete search history.

(56) References Cited

U.S. PATENT DOCUMENTS

| 2009/0130778 A1 | 5/2009 | Kalgutkar et al. |
| 2010/0167946 A1 | 7/2010 | Shaw et al. |
| 2010/0285505 A1 | 11/2010 | Ostermann et al. |
| 2011/0084199 A1* | 4/2011 | Pyo ............................... 250/216 |

OTHER PUBLICATIONS

Sönnichsen et al., "A molecular ruler based on plasmon coupling of single gold and silver nanoparticles", Nature Biotechnology, 2005, v. 23, No. 6, pp. 741-745.*
Liu et al. "Extinction coefficient of gold nanoparticles with different sizes and different capping ligands", Colloids and Surfaces B: Biointerfaces, 2007, v. 58, pp. 3-7.*
Sidorov in "Double Plasmon Resonance in Spherical Metal-Dielectric-Metal Nanostructures", Technical Physics, 2006, 2006, v. 51, No. 4, pp. 477-481.*

(Continued)

*Primary Examiner* — Yelena G Gakh
(74) *Attorney, Agent, or Firm* — Foley & Lardner LLP

(57) ABSTRACT

Technologies are generally described for providing and using a material including: a template molecule; a first cluster of one or more nanoparticles located at a first site on the template molecule; and a second cluster of one or more nanoparticles located at a second site on the template molecule and spaced apart from the first cluster. In some embodiments, the first and second clusters of nanoparticles exhibit a plasmon resonance having a first resonant peak and a second resonant peak.

7 Claims, 20 Drawing Sheets

(56) References Cited

OTHER PUBLICATIONS

Roy et al., "Double plasmonic profile of tryptophan-silver nanocrystals—Temperature sensing and laser induced antimicrobial activity", Photonics and Nanostructures—Fundamentals and Applications, 2012, v. 10, pp. 506-515.*

Biswas, H. et al., "Large broadband visible to infrared plasmonic absorption from Ag nanoparticles with a fractal structure embedded in a Tefton AF (R) matrix," Appl Phys Lett. 2006, vol. 88.

Chakravadhanula, V.S.K. et al., "Equal intensity double plasmon resonance of bimetallic quasi010nanocomposites based on sandwich geometry," Nanotechnology, 2008, vol. 19, pp. 225-302.

Kasthuri, J. et al., "Functionalization of silver and gold nanoparticles using amino acid conjugated bile salts with tunable longitudinal plasmon resonance," Colloids and Surfaces B. Biointerfaces, 2009, vol. 73, No. 2, pp. 387-393.

Kreibig, U. et al., "Optical Properties of Metal Clusters," Springer, 1995.

Roy S. et al., "Nanoparticle induced conformational change in DNA and chirality of silver nanoclusters," J. Nanosci. Nanotechnol., 2010, vol. 10, No. 2, pp. 819-825.

Sarkar, T. et al., "Thermal Hysteresis of Some Important Physical Porpoerties of Nanoparticles," JCIS, 2008, vol. 327, pp. 224-232.

International Search Report and Written Opinion for PCT/IB2011/001392, DTD Nov. 21, 2011.

Kah, J.C.Y., et al. 'Early diagnosis of oral cancer based on the surface plasmon resonance of gold nanoparticles', International Journal of Nanomedicine, 2007, vol. 2 (4), pp. 785-798.

* cited by examiner

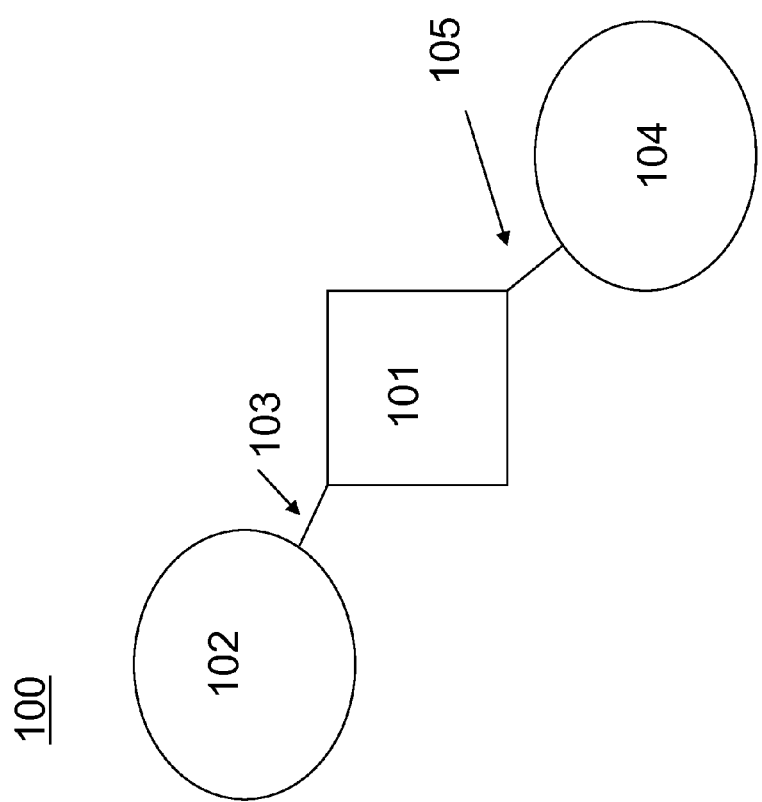

```
nano_peaks function [lam1,od1,lam2,od2]=nano_peaks(spectra)

x=spectra(:,1);
y=spectra(:,2);

xx=linspace(min(x),max(x),100);
yy=spline(x,y,xx);

i=findpeaks(yy);
xxx=xx(i);
yyy=yy(i);

k=find(xxx>375 & xxx<425);
l=find(xxx>490 & xxx<550);

if length(yyy(k))>=2
    kk=find(yyy(k)==max(yyy(k)));
    od1=yyy(kk);od1=od1(1)
    lam1=xxx(kk);lam1=lam1(1);
else
    lam1=xxx(k);
    od1=yyy(k);
end if length(yyy(l))>=2
    ll=find(yyy(l)==max(yyy(l)));
    od2=yyy(ll);
    lam2=xxx(ll);
else
    lam2=xxx(l);lam2=lam2(1);
od2=yyy(l);od2=od2(1);
end
```

Fig. 11A

```
findpeaks function ind = findpeaks(varargin)
% FINDPEAKS Find peaks in real vector.
% IND=FINDPEAKS(Y) finds the indices (IND) which are local maxima in the sequence Y.
% If want to find valleys instead of peaks, use IND=FINDPEAKS(-Y).
% Marcos Duarte mduarte@usp.br 11oct1998 y=varargin{1};
switch length(y)
case 0
    ind = [];
case 1
    ind = 1;
otherwise
    if size(y,2) == 1, y=y'; end
    dy = diff(y);
    ind = find( ([dy 0]<0) & ([0 dy]>=0) );  %or you can try: ind = find( ([dy 0]<0) & ([0 dy]>0) );
    % ind does not return the first and last values in case they are maxima.
    % If you want the possibility of the first and last values
    % be considered as peaks, comment this line:
    if ind(1) == 1, ind(1) = []; end
    % and uncomment this line:
    %if y(end-1)<y(end), ind = [ind length(y)]; end
```

Fig. 11B

NANO SENSING OF TEMPERATURE USING EQUAL INTENSITY DOUBLE PLASMON RESONANCE (EIDPR)

CROSS-REFERENCE TO RELATED APPLICATION

The present application claims priority to a corresponding patent application filed in India and having application number 375/KOL/2011, filed on Mar. 21, 2011, the entire contents of which are herein incorporated by reference.

BACKGROUND

A plasmon is a quantum of plasma oscillation. The plasmon is a quasiparticle resulting from the quantization of plasma oscillations just as photons and phonons are quantizations of light and mechanical vibrations, respectively. Thus, plasmons are collective oscillations of the free electron gas density, for example, at optical frequencies. Plasmons can couple with a photon to create another quasiparticle called a plasma polariton. Since plasmons are the quantization of classical plasma oscillations, many of their properties can be derived directly from Maxwell's equations.

Surface plasmons are those plasmons that are confined to surfaces and that interact strongly with light resulting in a polariton. They occur, for example, at the interface of a vacuum or material with a positive dielectric constant, and a negative dielectric constant (e.g., a metal or doped dielectric).

The excitation of surface plasmons by light is referred to as a surface plasmon resonance for planar surfaces or localized surface plasmon resonance for nanometer-sized structures. A surface plasmon resonance may influence the spectral characteristics (e.g., absorbance, reflectance, or emittance) of a material.

Unless otherwise indicated herein, the materials described in this section are not prior art to the claims in this application and are not admitted to be prior art by inclusion in this section.

SUMMARY

In one aspect, a material is disclosed including: a template molecule; a first cluster of one or more nanoparticles located at a first site on the template molecule; and a second cluster of one or more nanoparticles located at a second site on the template molecule and spaced apart from the first cluster. In some embodiments, the first cluster of nanoparticles exhibit a plasmon resonance having a first resonant peak, and the second cluster of nanoparticles exhibit a plasmon resonance having a second resonant peak.

In some embodiments, at least one of the first cluster and the second cluster includes a metallic nanoparticle. In some embodiments, the first cluster includes a metallic nanoparticle including a first metallic material, and the second cluster includes a second type of metallic nanoparticle including a second metallic material. In some embodiments, the first metallic material is different from the second metallic material. In some embodiments, the first metallic material is the same or substantially the same material as the second metallic material. In some embodiments, the metallic nanoparticle includes a silver or gold nanoparticle.

In some embodiments, the template molecule includes an organic molecule having at least two nitrogen centers spaced apart by one or more carbon bonds, and where each of the first and second sites corresponds to a respective nitrogen center. In some embodiments, the template molecule includes tryptophan.

In some embodiments, a property of the plasmon resonance depends on a condition of a local environment of the material. In some embodiments, the condition of the local environment includes a local temperature. In some embodiments, the property of the plasmon resonance includes at least one selected from the list consisting of: a wavelength the first resonant peak; a wavelength of the second resonant peak; an extinction coefficient associated with the first resonant peak; and an extinction coefficient associated with the second resonant peak.

In some embodiments, the first resonant peak and second resonant peak have substantially equal intensities.

In some embodiments, at least one property of the first resonant peak exhibits a dependence on a condition of the local environment which is different from the dependence of at least one property of the second resonant peak on the condition of the local environment.

In some embodiments, the first resonant peak and second resonant peak correspond to wavelengths in the visible or near-infrared spectrum.

In another aspect, a method of detecting a condition of an environment is disclosed, the method including: introducing a material to the environment, where the material includes: a template molecule; a first cluster of one or more nanoparticles located at a first site on the template molecule; and a second cluster of one or more nanoparticles located at a second site on the template molecule and spaced apart from the first cluster. In some embodiments, the first cluster of nanoparticles exhibit a plasmon resonance having a first resonant peak, and the second clusters of nanoparticles exhibit a plasmon resonance having a second resonant peak. The method may also include detecting at least one property of the plasmon resonance of the material and determining information indicative of the condition of the environment based on the at least one detected property of the plasmon resonance of the material.

In some embodiments, the first cluster includes a metallic nanoparticle including a first metallic material, and the second cluster includes a second type of metallic nanoparticle including a second metallic material. In some embodiments, the first metallic material is different from the second metallic material. In some embodiments, the first metallic material is the same or substantially the same material as the second metallic material.

In some embodiments, the condition includes a local temperature of the environment. In some embodiments, the environment includes an intracellular environment and the condition includes an intracellular temperature.

In some embodiments, the at least one property of the plasmon resonance of the material includes at least one, at least two, or at least three different property or properties selected from the list consisting of: a wavelength of the first resonant peak; a wavelength of the second resonant peak; an extinction coefficient associated with the first resonant peak; and an extinction coefficient associated with the second resonant peak.

In some embodiments, the at least one property of the plasmon resonance of the material includes a wavelength of the first resonant peak; a wavelength of the second resonant peak; an extinction coefficient associated with the first resonant peak; and an extinction coefficient associated with the second resonant peak.

In some embodiments, detecting at least one property of the plasmon resonance of the material includes detecting an absorbance spectrum of the material.

In some embodiments, at least one of the first cluster and second cluster includes a metallic nanoparticle (e.g., a silver or gold nanoparticle).

In some embodiments, the template molecule includes an organic molecule having at least two nitrogen centers spaced apart by one or more carbon bonds, and where each of the first site and the second site corresponds to a respective nitrogen center.

Some embodiments include outputting information indicative of the condition of the environment.

In some embodiments, the template molecule includes tryptophan.

In some embodiments, the first resonant peak and the second resonant peak correspond to wavelengths in the visible or near-infrared spectrum.

In another aspect, an apparatus for detecting a condition of an environment is disclosed, the apparatus including: a material configured for introduction to the environment. In some embodiments, the material includes: a template molecule; a first cluster of one or more nanoparticles located at a first site on the template molecule; and a second cluster of one or more nanoparticles located at a second site on the template molecule and spaced apart from the first cluster. In some embodiments, the first cluster of nanoparticles exhibit a plasmon resonance having a first resonant peak, and the second cluster of nanoparticles exhibit a plasmon resonance having a second resonant peak. In some embodiments, the apparatus includes a detector configured to detect at least one property of the plasmon resonance of the material while the material is in the environment.

In some embodiments, the first cluster includes a metallic nanoparticle including a first metallic material, and the second cluster includes a second type of metallic nanoparticle including a second metallic material. In some embodiments, the first metallic material is different from the second metallic material. In some embodiments, the first metallic material is the same or substantially the same material as the second metallic material.

Some embodiments include a processor in communication with the detector and configured to determine information indicative of the condition of the environment based on the at least one detected property of the plasmon resonance of the material. Some embodiments include an output coupled to the processor for outputting information indicative of the condition of the environment.

In some embodiments, the at least one property of the plasmon resonance of the material includes at least one, at least two, or at least three property or properties selected from the list consisting of: a wavelength of the first resonant peak; a wavelength of the second resonant peak; an extinction coefficient associated with the first resonant peak; and an extinction coefficient associated with the second resonant peak.

In some embodiments, the at least one property of the plasmon resonance of the material includes a wavelength of the first resonant peak; a wavelength of the second resonant peak; an extinction coefficient associated with the first resonant peak; and an extinction coefficient associated with the second resonant peak.

In some embodiments, the detector includes a spectrometer configured to detect an absorbance spectrum of the material. In some embodiments, the first resonant peak and the second resonant peak correspond to wavelengths in the visible or near-infrared spectrum. In some embodiments, the absorbance spectrum is detected over multiple wavelengths which include wavelengths corresponding to the first resonant peak and the second resonant peak.

In some embodiments, at least one of the first cluster and second cluster includes a metallic nanoparticle (e.g., a gold or silver nanoparticle).

In some embodiments, the template molecule includes an organic molecule having at least two nitrogen centers spaced apart by one or more carbon bonds, and where each of the first site and second site corresponds to a respective nitrogen center. In some embodiments, the template molecule includes tryptophan.

In another aspect, a method is disclosed of making a plasmon resonance material, the method including: providing a template molecule; forming a first cluster of one or more nanoparticles located at a first site on the template molecule; and forming a second cluster of one or more nanoparticles located at a second site on the template molecule and spaced apart from the first cluster such that the first cluster exhibits a plasmon resonance having a first resonant peak, and the second cluster exhibits a plasmon resonance having a second resonant peak.

In some embodiments, the first cluster includes a metallic nanoparticle including a first metallic material and the second cluster includes a second type of metallic nanoparticle including a second metallic material. In some embodiments, the first metallic material is different from the second metallic material. In some embodiments, the first metallic material is the same or substantially the same material as the second metallic material.

In some embodiments, the template molecule includes at least a first site and a second site which are spaced apart. In some embodiments, the one or more nanoparticles that form the first cluster and the second cluster have an affinity for the first site and the second site. Some embodiments include forming the first cluster and the second cluster includes introducing nanoparticles to the template molecule that are attracted to the first site and the second site.

In some embodiments, the at least one of the first cluster and second cluster includes a metallic nanoparticle (e.g., a gold or silver nanoparticle).

In some embodiments, the template molecule includes an organic molecule having at least two nitrogen centers spaced apart by one or more carbon bonds, and where each of the first site and second site corresponds to a respective nitrogen center. In some embodiments, the template molecule includes tryptophan.

Some embodiments include reducing a silver salt with a reducing agent in the presence of the template molecule. In some embodiments, the silver salt includes silver nitrate. In some embodiments, the reducing agent includes sodium borohydride. In some such embodiments, the template molecule includes tryptophan.

In some embodiments, the method includes providing a solution of tryptophan and silver nitrate ($AgNO_3$); cooling the solution; adding sodium borohydride ($NaBH_4$) to form a reaction mixture; and agitating the reaction mixture. In some embodiments, cooling the solution includes cooling the solution to a temperature of about 4° C.

In some embodiments, the step of adding $NaBH_4$ to form a reaction mixture includes adding $NaBH_4$ at a ratio of about 1:80 ($AgNO_3$:$NaBH_4$).

In some embodiments, the first resonant peak and the second resonant peak correspond to wavelengths in the visible or near-infrared spectrum.

In another aspect, a method is disclosed including: providing a substance for analysis; conjugating nanoparticles to the substance to form a nanoparticle conjugated material; detecting a spectral property of the material; determining information indicative of the composition of the substance based on the detected spectral property.

In some embodiments, the determining information step includes determining if the material exhibits a double plasmon resonance. In some embodiments, the conjugating step includes: forming a solution of the substance and $AgNO_3$; cooling the solution; adding $NaBH_4$ to form a reaction mixture; and agitating the reaction mixture. In some embodiments, the cooling step includes cooling the solution to a temperature of about 4° C. In some embodiments, the adding $NaBH_4$ step includes adding $NaBH_4$ at a ratio of about 1:80 ($AgNO_3$:$NaBH_4$).

In some embodiments, the information indicative of the composition of the substance includes information indicative of the presence of tryptophan in the substance.

Various embodiments may include any of the forgoing materials, devices, techniques, etc. either alone or in any suitable combination.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1 is a schematic illustrating an example of a resonant material (as shown, a double resonant material);

FIG. 11A and FIG. 11B are MATLAB scripts used in the generation of FIGS. 9 and 10;

DETAILED DESCRIPTION

Figure 2B:
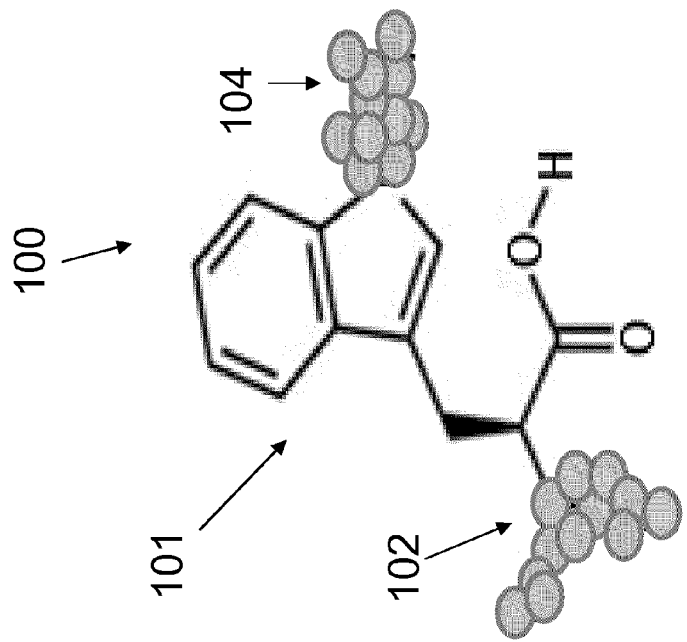
FIG. 2B is an illustration of a resonant material featuring the template molecule of FIG. 2A.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Methods, apparatus, systems, devices, and computer program products related to resonant materials and detection schemes employing these materials are disclosed. As described herein, materials may be provided which exhibit a resonant (e.g., wavelength dependent) response to incident light which depends on some property (e.g., temperature) of the material's environment. Accordingly, the material may be used to sense, measure, detect, etc.; this property or changes thereof. For example, the resonant material may exhibit a color change in response to a change in temperature.

In some embodiments, the materials described herein may feature a nanoscale "sandwich" structure which gives rise to a more complicated resonant response (e.g., featuring two or more resonant response peaks) than that found in materials having a different morphology. In some embodiments, this more complicated response may be advantageously exploited to provide robust sensing. For example, the "sandwich" resonant material may exhibit a more vivid color change in response to a change in temperature than corresponding materials lacking the sandwich structure.

Briefly stated, technologies are described for providing and using a material including: a template molecule; a first cluster of one or more nanoparticles located at a first site on the template molecule; and a second cluster of one or more nanoparticles located at a second site on the template molecule and spaced apart from the first cluster. In some embodiments, the first and second clusters of nanoparticles exhibit a plasmon resonance having a first resonant peak and a second resonant peak FIG. 1 shows a schematic diagram of a resonant material 100. The resonant material 100 includes a template molecule 101, a first cluster 102 of one or more nanoparticles located at a first site 103 on the template molecule 101 and a second cluster 104 of one or more nanoparticles located at a second site 105 on the template molecule 101. The first and second clusters 102 and 104 of nanoparticles are spaced apart from each other, e.g. by a distance of about 100 nm or less, about 50 nm or less, about 10 nm or less, about 1 nm or less, about 0.1 nm or less etc., e.g., in the range of about 0.1-1.0 nm or about 0.1-10 nm. As will be discussed in detail below, this so called "sandwich structure" arrangement of the two clusters 102 and 104 of nanoparticles spaced apart from each other may result in the resonant material 100 exhibiting a plasmon resonance, e.g., a double plasmon resonance characterized by at least two resonant peaks. The clusters 102 and 104 may be made up of any suitable nanoparticle. In some embodiments, the nanoparticles may be metallic, for example noble metallic (e.g., silver or gold) nanoparticles. The nanoparticles may be generally spherical in shape, having a diameter of about 1000 nm or less, about 500 nm or less, about 200 nm or less, about 100 nm or less, about 50 nm or less, about 10 nm or less, etc., e.g., in the range of about 1-100 nm.

Clusters 102 and 104 may be made of the same or different materials. In some embodiments, the clusters 102 and 104 may be made of different types of metallic material. For example, cluster 102 may be a cluster primarily composed of gold nanoparticle while the cluster 102 is a cluster primarily composed of silver nanoparticles.

In some embodiments, the nanoparticles of the clusters 102 and 104 may exhibit properties not found in the corresponding bulk material. For example, noble metallic nanoparticles with diameters much smaller than the wavelength of the exciting light may exhibit strong absorption maxima due to collective resonant oscillations of the conduction electrons, i.e., a localized surface plasmon resonance, which may occurs, for example, in the visible region or the near infrared region of the optical spectrum.

In some embodiments (e.g., embodiments where clusters 102 and 104 are formed of the same type of material), the template molecule 101 includes two sites 103 and 105 having a similar affinity for a type of nanoparticle (e.g., a silver nanoparticle). As described in greater detail below, such molecule can serve as a basis for the formation of the sandwich structure of material 100 where the clusters 102 and 104 are spaced apart from each other, as shown in FIG. 1.

In some embodiments, the affinity centers have a lone pair of electrons. For example, the affinity center may have a nitrogen, sulfur, or oxygen atom. In some embodiments, the affinity center is a primary, second, or tertiary amine, a cyclic amine, or an aromatic amine.

For example, in some embodiments, the template molecule have an amine ($NH_2$), a monoalkyl amine (NHR), a dialkylamine (NRR'), a piperidine, or a pyridine group, or two or more of such groups. In some embodiments, the template molecule is an amino acid such as, but not limited to, e.g., tryptophan, methionine, arginine, lysine, glutamine, cysteine, asparagine, a bipyridine such as 2,2'-bipyridine, 3,3'-bipyridine, 4,4'-bipyridine, or 2,4'-bipyridine, a diaminobiphenyl such as 4,4'-diaminobiphenyl or 2,2'-diaminobiphenyl.

In some embodiments, the template molecule comprises an organic molecule. In some embodiments, the molecule may have at least two affinity centers (e.g., nitrogen centers) spaced apart by one or more carbon bonds. The affinity centers (e.g., nitrogen centers) attract nanoparticles, resulting in the formation of the clusters 102 and 104 on resonant material 100. Accordingly, the affinity centers correspond to the sites 103 and 105 of the clusters 102 and 104.

In some embodiments, the template molecule 101 does not include any additional centers having substantial affinity to nanoparticles of the type found in the clusters 102 and 104. In some embodiments, this ensures that the resulting resonant material 100 exhibits the sandwich structure described above.

Figure 3:
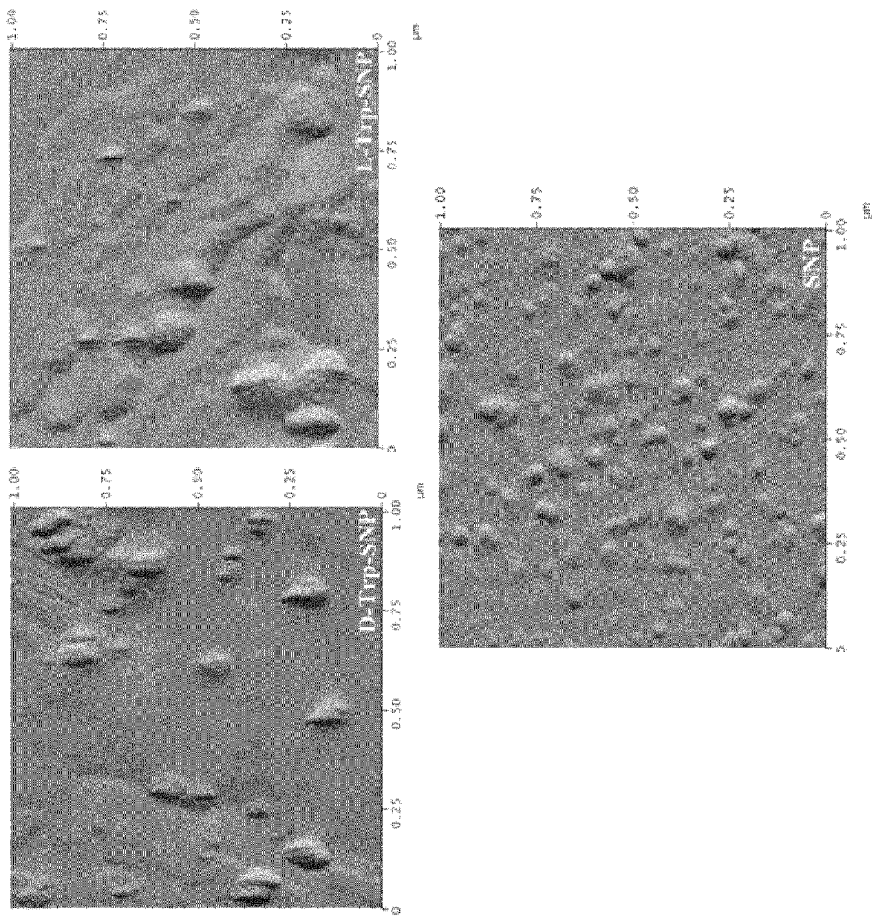
FIG. 3 shows atomic force microscope (AFM) images, the upper left panel shows silver nanoparticles (SNP) conjugated to the D-stereoisomer of tryptophan; the upper right panel shows SNP conjugated to the L-stereoisomer of tryptophan, the lower panel shows bare SNP.

FIG. 3 shows atomic force (AFM) microscope images which illustrates the sandwich structured of one embodiment of resonant material 100 having an enantiomeric template molecule to which silver nanoparticles (SNP) have conjugated. Referring still to FIG. 3, the upper left panel shows a nanoparticles conjugated to the D-stereoisomer of a template molecule, the upper right panel shows nanoparticles conjugated to the L-stereoisomer of tryptophan. The lower panel shows unconjugated nanoparticles. Note that the template conjugated materials exhibit an asymmetric morphology, corresponding to the sandwich structure described above. In contrast, the unconjugated nanoparticle clusters are roughly symmetric, indicating a lack of sandwich structure.

Resonant material 100 exhibits a resonant response to incident light which depends on one or more properties of the incident light (e.g., wavelength, polarization, intensity, etc.). In the non-limiting examples that follow, the property will be the wavelength of the incident light. In some embodiments, the resonant material 100 will preferentially absorb light at one or more resonant wavelengths.

Figure 4A:
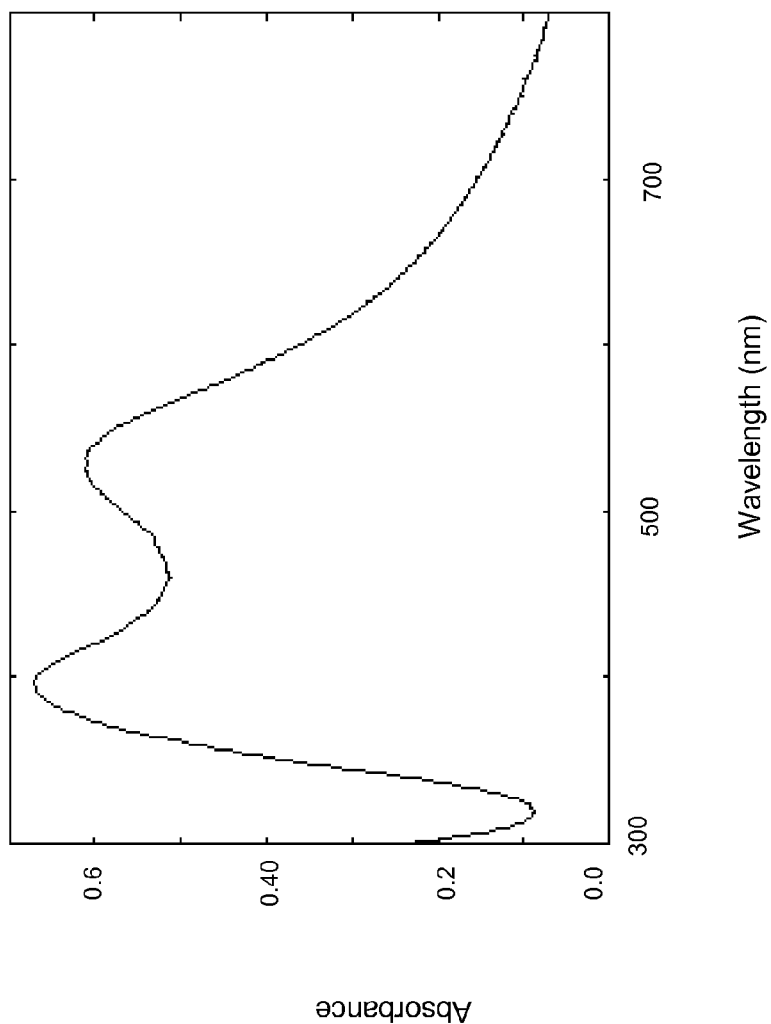
FIG. 4A is a plot of absorbance vs wavelength for a resonant material featuring silver nanoparticles a sandwich structure configuration.

For example, FIG. 4A shows a plot of absorbance as a function of wavelength (nm) for a resonant material 100. The plot includes two peaks, corresponding to a pair of resonant wavelengths $\lambda_1$ (the lower wavelength peak) and $\lambda_2$ (the higher wavelength peak), referred to as a double resonance (DR). In the case where the strength the resonant peak are similar (e.g., where the absorbance peaks values differ by less that 25%, less than 20%, less than 15%, less than 10%, less than 5%, less than 15, etc., e.g., in the range of 0-10%), the resonance may be referred to a an equal intensity double plasmon resonance (EIDPR) This double resonant behavior may correspond to a surface plasmon resonance of the clusters 102 and 104 of nanoparticles in the sandwich configuration.

Figure 4B:
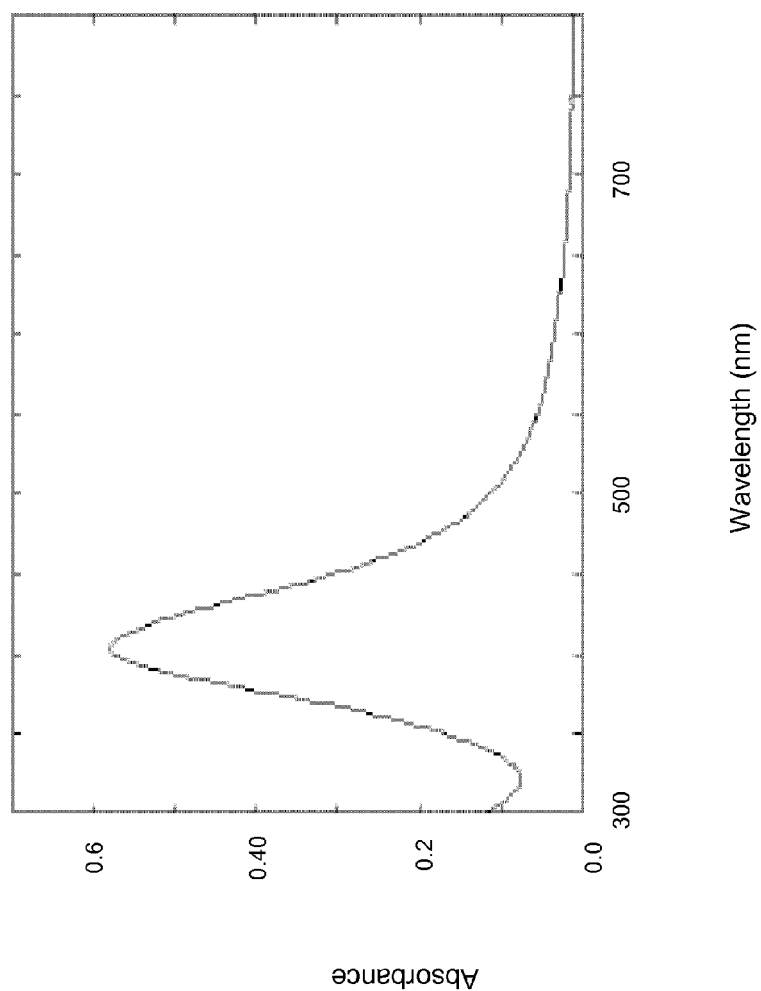
FIG. 4B is a plot of absorbance vs wavelength for a resonant material featuring bare silver nanoparticles.

The double resonance behavior of resonant material 100 may differ significantly from the resonant behavior exhibited by bare clusters of corresponding nanoparticles (i.e., material lacking the sandwich structure). FIG. 4B shows a plot of absorbance as a function of wavelength for bare nanoparticle clusters. Note that the plot includes only a single resonant peak.

Figure 4C:
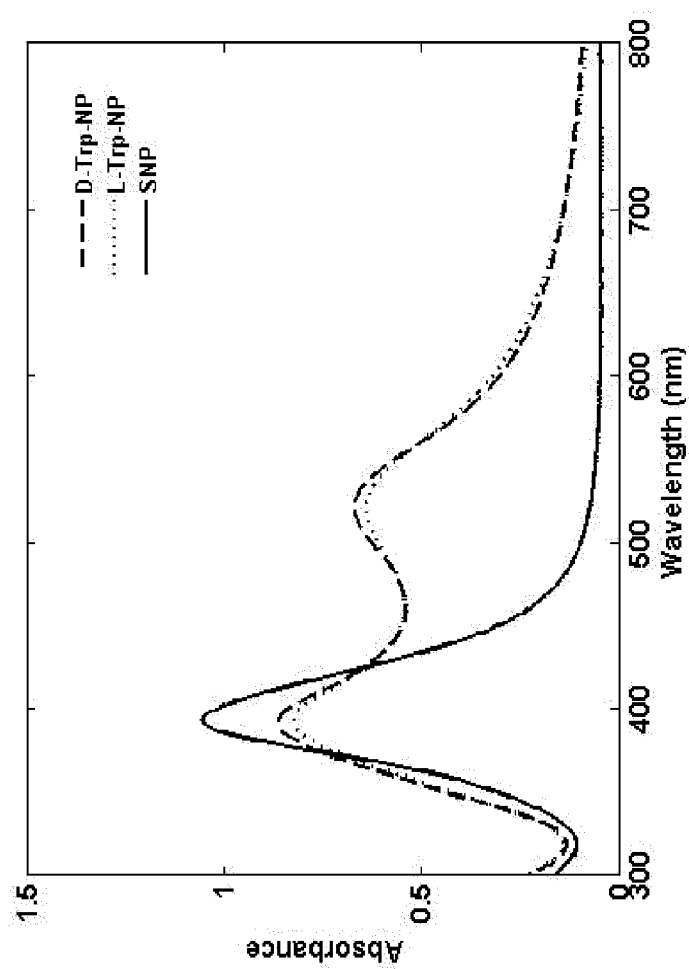
FIG. 4C is a comparison plot of absorbance vs wavelength for resonant materials.

Similarly, FIG. 4C shows a comparison of plots of absorbance versus wavelength for nanoparticles conjugated to the D-stereoisomer of a template molecule, nanoparticles conjugated to the L-stereoisomer of a template molecule, and unconjugated nanoparticles. Both forms of templated structures exhibit the EIDPR, while the unconjugated nanoparticles exhibit only a single resonant peak.

One or more properties of the resonant behavior of resonant material 100 may depend on a condition the environment of the material, e.g., the local environment in which the template molecule 101 and clusters 102 and 104 are found. The condition may be a local temperature, a condition of a local chemical environment (e.g., pH level, presence of a particular substance, etc.), or any other suitable condition.

The property may include the wavelength of a resonant peak, the intensity of a resonant peak, the width of a resonant peak, the rate of change of the foregoing, or combinations thereof.

Figures 5A, 5B:
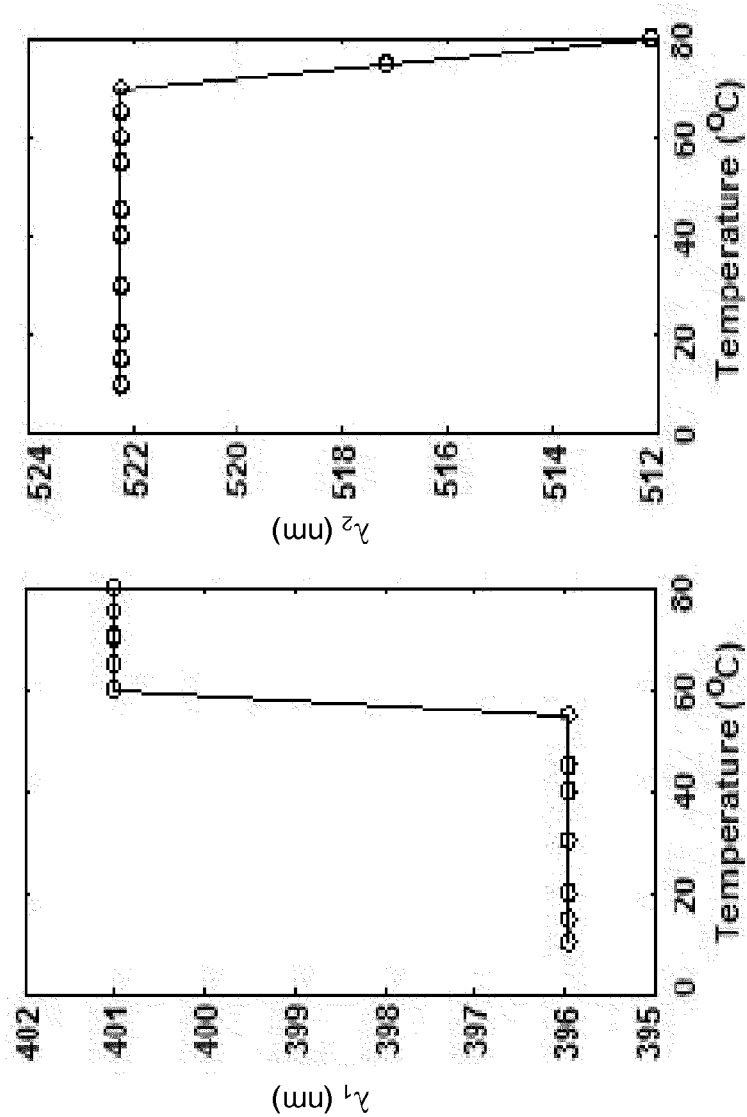
FIG. 5A and FIG. 5B are plots of peak wavelength vs temperature for a resonant material featuring a double resonance.
Figure 5C:
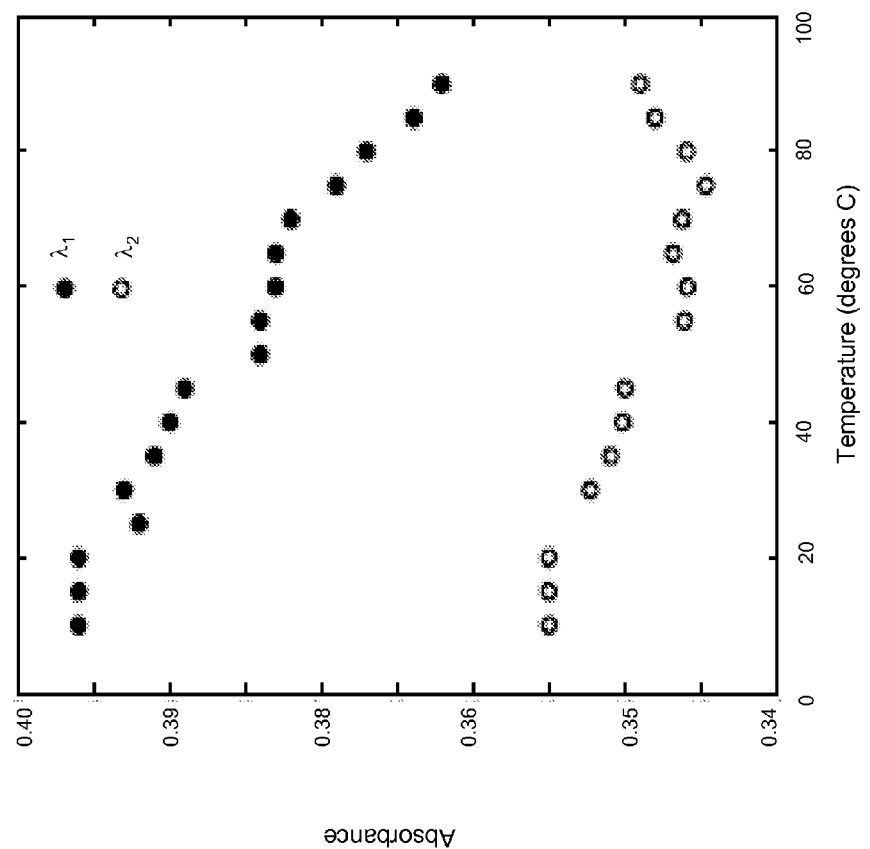
FIG. 5C is a plot of absorbance versus temperature at each of two peak wavelengths for a resonant material featuring a double resonance.

In embodiments where resonant material 100 exhibits a double plasmon resonance, properties of the two resonant peaks may exhibit differing dependence on a given environmental property (e.g., temperature). For example, FIG. 5A and FIG. 5B show plots of the dependence of the resonant wavelengths $\lambda_1$ and $\lambda_2$ as a function of temperature for a resonant material 100 which exhibits an EIDPR (as shown in FIG. 4A). Note that $\lambda_1$ varies most strongly with temperature in a first temperature range (as shown, the range of 55-60° C.), while $\lambda_2$ varies most strongly with temperature in a second temperature range (as shown, the range of 70-80° C.). FIG. 5C shows a plot of absorbance at each peak wavelength ($\lambda_1$ (solid circle) and $\lambda_2$ (open circle)) as a function of temperature for the same material. Note that the rate change in absorbance as a function of temperature may differs for the two peaks. For example, as shown, the peak at $\lambda_2$ exhibits a more rapid extinction as the temperature is increased from 0-100° C. As will be discussed greater detail below, this dependence may be used in sensing applications, e.g., to provide robust sensing of temperature.

Figure 6:
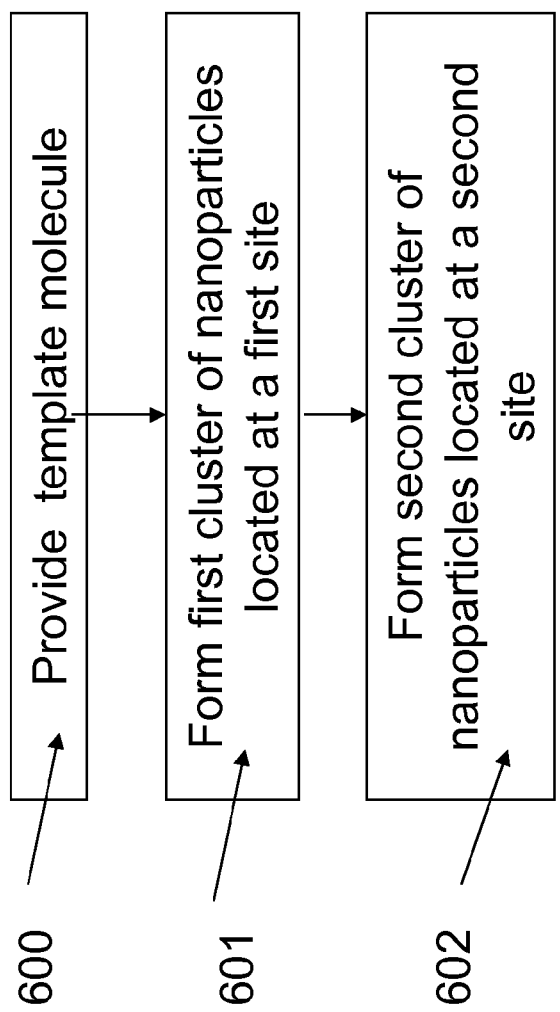
FIG. 6 is a process flow illustrating a method of making a resonance material.

FIG. 6 shows a process flow for an illustrative method of making a resonant material 100 of the type described herein. In an operation 600, a template molecule 101 (e.g., tryptophan) is provided. In some embodiments, the template molecule 101 includes at least a first site 103 and a second site 105 which are spaced apart. In operations 601 and 602, clusters of nanoparticles 102 and 104 are formed at sites 103 and 105, e.g., resulting in a resonant material 100 as shown in FIG. 1. Operations 601 and 602 may be performed simultaneously, stepwise with operation 601 being performed prior to operation 602, or stepwise with operation 602 being performed prior to operation 601.

In some embodiments, the operations 601 and 602 of forming nanoparticle clusters includes introducing nanoparticles to the template molecule which are attracted to the sites 103 and 105 to form spaced apart clusters 102 and 104. In some embodiments, the nanoparticles are introduced to the template molecule by reducing a salt of a metal (or other material) with a reducing agent in the presence of the template molecule. In some embodiments, the salt may be a salt of a noble metal, e.g., a silver salt.

Note that the above described reaction does not require the synthesis of nanostructures having more complicated morphology than nanoparticles (e.g., nanorods) in order to obtain a material which exhibits a double resonance. Instead, the reaction results in bi-directional growth of silver nanoparticles resulting in a sandwich structure and corresponding double resonance behavior described above.

Figure 8:
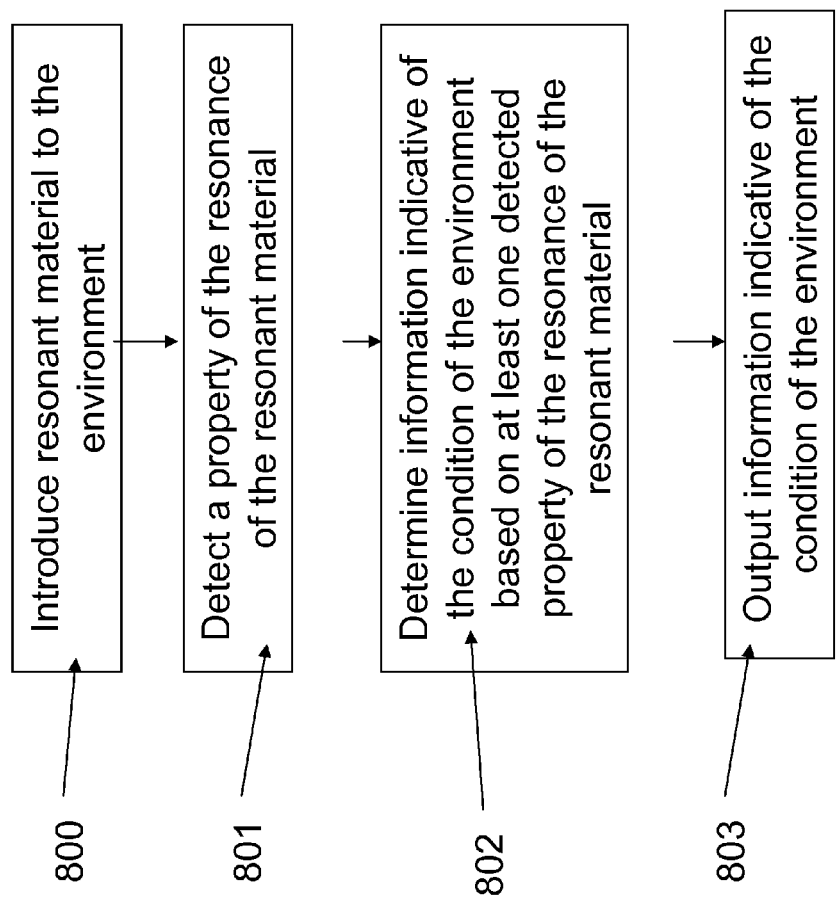
FIG. 8 is a process flow illustrating a detection method.

FIG. 8 illustrates a method of detecting a condition of an environment using a resonant material of the type described herein. In operation 800, the resonant material is introduced into the environment. In some embodiments, a suspension (e.g., a colloidal suspension) of the resonant material is formed (e.g., using any suitable technique known in the art) and introduced into the environment. In one embodiment, the material may be introduced into the intracellular environment of a microorganism.

In operation 801, a property of the resonance of the resonant material is detected. In some embodiments, the detection may simply be a visual inspection of the color of the material. For example, when the resonant material is an EIDPR material formed by templating silver nanoparticles on tryptophan (e.g., as described in the Examples below), temperature changes may result in a visible change of a reddish purple hue of the material. In contrast, bare silver nanoparticles typically have a yellow color which does not visibly change with temperature.

In some embodiments, the detection may include detection of an optical property of the material (e.g., absorbance) at one or more wavelengths. In some embodiments, the detection may include detections at multiple times, multiple locations, or combinations thereof. For example, in some embodiments, an absorbance spectrum (sometimes referred to in the art as an extinction spectrum) of the material is detected.

In various embodiments, the detected property of the resonance of the material includes a wavelength of one or more resonant peaks, the intensity of one or more resonant peaks, an extinction coefficient associated with a resonant peak (i.e., a value related to the change in intensity of a resonant peak as a function of some parameter) of the first resonant peak; or any other suitable property. In some embodiments, multiple different properties are detected (e.g., at least two or at least three, different properties). As described in greater detail below, in some embodiments, detection of multiple different resonant properties results in more accurate or robust detection of the environmental condition.

In operation 802, information indicative of the condition of the environment is determined based on at least one detected property of the resonance of the material. In some embodiments, the determination may be made by visual inspection, e.g., by comparison of the color of the material to an exemplar showing the relationship between material color and a condition, e.g., temperature. In some embodiments, the property of the resonant material detected in step 801 may be processed, e.g., using software running on a microprocessor, to determine the condition of the environment.

In operation 803, information indicative of the condition of the environment is output using any suitable output device, e.g., a video monitor. The information may be displayed to a user or operator.

In one embodiment, the resonant material may be tryptophan conjugated SNP featuring an EIDPR, as described above. The sensitivity of the EIDPR to temperature makes this nano-configuration suitable for a thermal sensor. The two resonant peaks ($\lambda_1$ and $\lambda_2$) at 393 nm and 520 nm (e.g., as shown in FIG. 4C) exhibit substantial variation with respect to temperature ranging, e.g., from 10 to 90° C. In other embodiments, other suitable EIDPR materials may be used/

Figure 9:
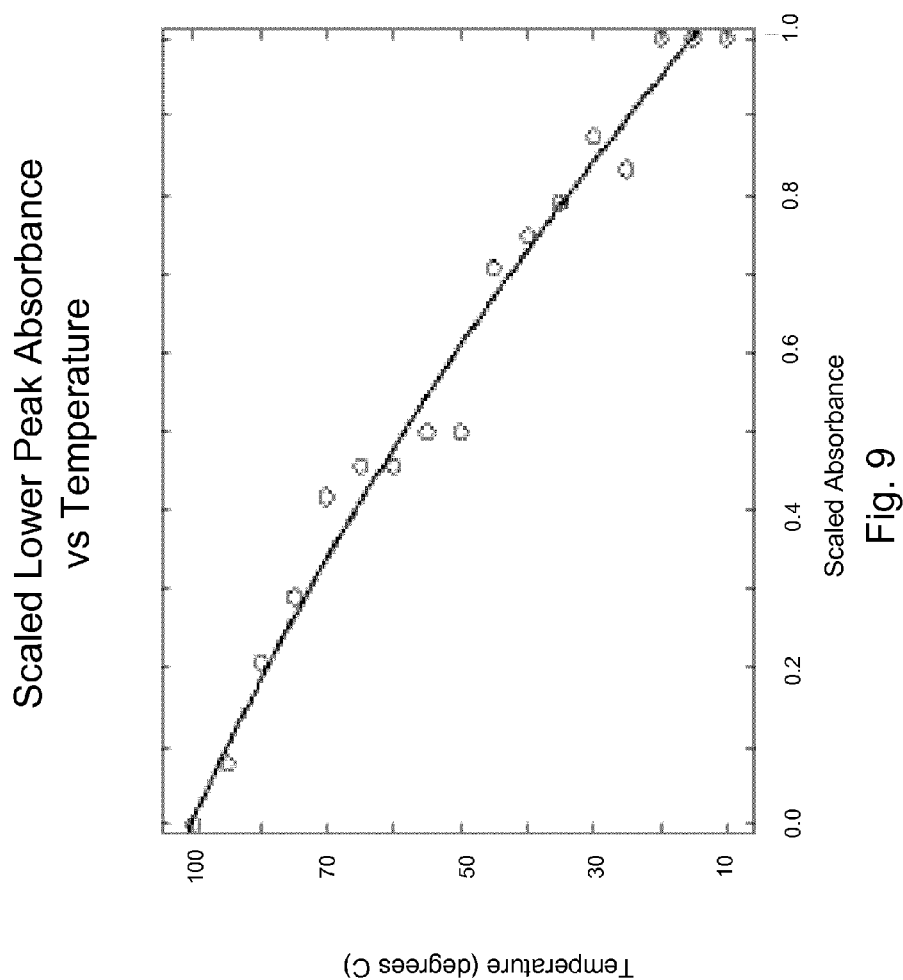
FIG. 9 is a plot of scaled peak absorbance vs temperature for a resonant material.

In some embodiments, the lower wavelength absorbance maximum may be chosen as it is more sensitive to temperature. The response of lower peak wavelength with temperature is shown in FIG. 9. As shown, the change of absorbance at lower wavelength is scaled up with the following normalization procedure where absorbance is transformed with the following scaling equation:

$$OD_t = \frac{OD - \text{Min}(OD)}{\text{Max}(OD) - \text{Min}(OD)}$$

where $OD_t$ represents the transformed absorbance value at a given temperature t. Min(OD) and Max(OD) refer to the minimum and maximum absorbance values over the temperature range. Such normalized absorbance is referred as scaled absorbance for the sake of simplification. As seen from this figure it is found that there exists a linear response of temperature with the absorbance and for the wide range of temperature the normalized absorbance approaches one.

Figure 10:
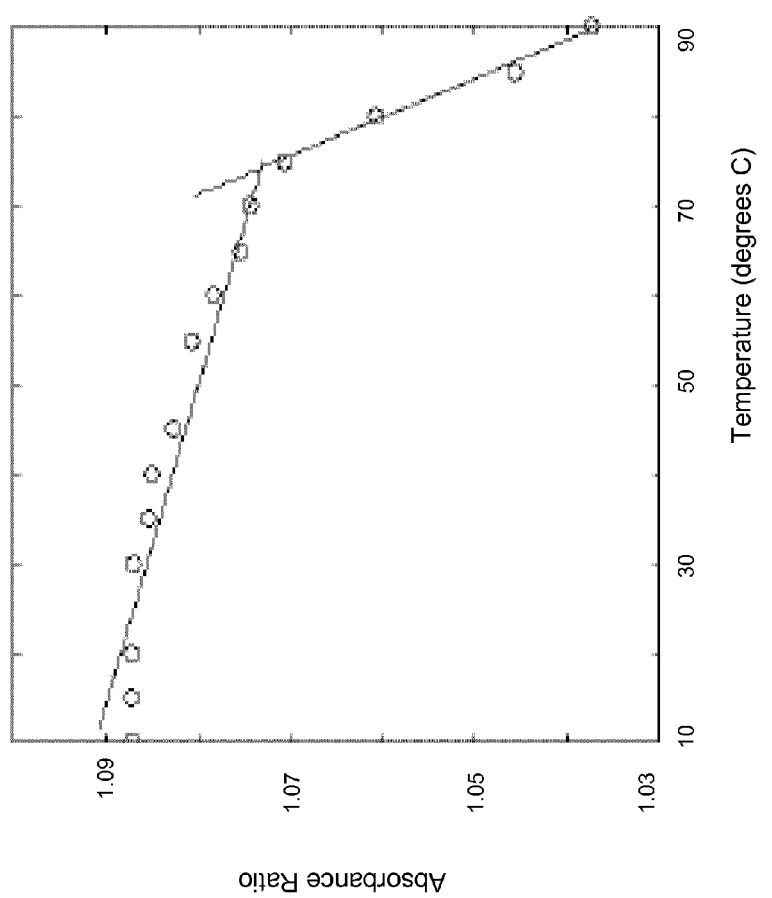
FIG. 10 is a plot of peak absorbance ratio vs temperature for a resonant material.

FIG. 10 shows a plot of the absorbance ratio (OD1/OD2) of absorbance value of the peaks ($\lambda_1$ and $\lambda_2$) of the respective two plasmon maxima versus temperature. OD1 is the absorbance at $\lambda_1$ and OD2 is the absorbance at $\lambda_2$. Note that two distinct linear zones of temperature dependence are obtained. The higher temperature zone (>65° C.) is more sensitive to temperature.

In some embodiments, the temperature sensitivity is unidirectional in nature, as decreasing temperature does not cause appreciable decrease in the absorbance. In some embodiments, an irreversible distortion of the sandwich structure of the resonant material in response to increased temperature may be responsible for this result. It may be noted that, in some embodiments, as the temperature is raised above a particular temperature, the double plasmon nature may be reduced or eliminated. In some embodiments, the unidirectional temperature dependence can be exploited in maintaining the thermal history (as it only records the rise of temperature).

As will be understood by those skilled in the art, the plots found in FIGS. 9 and 10 may be generated by obtaining absorption spectra for the resonant material for multiple temperatures over a given range. The absorption spectra can be processed to determine temperature dependence the wavelengths ($\lambda_1$ and $\lambda_2$) and values (OD1 and OD2) of the resonance peaks of the spectra. In various embodiments, any suitable peak detection algorithm known in the art may be used. FIG. 11A and FIG. 11B show exemplary peak detection algorithms (presented in the well know MATLAB® programming language available from MathWorks of 3 Apple Hill Drive, Natick Mass.) suitable for producing the plots shown in FIGS. 9 and 10. Alternatively, peaks may be detected manually "by eye".

Figure 12:
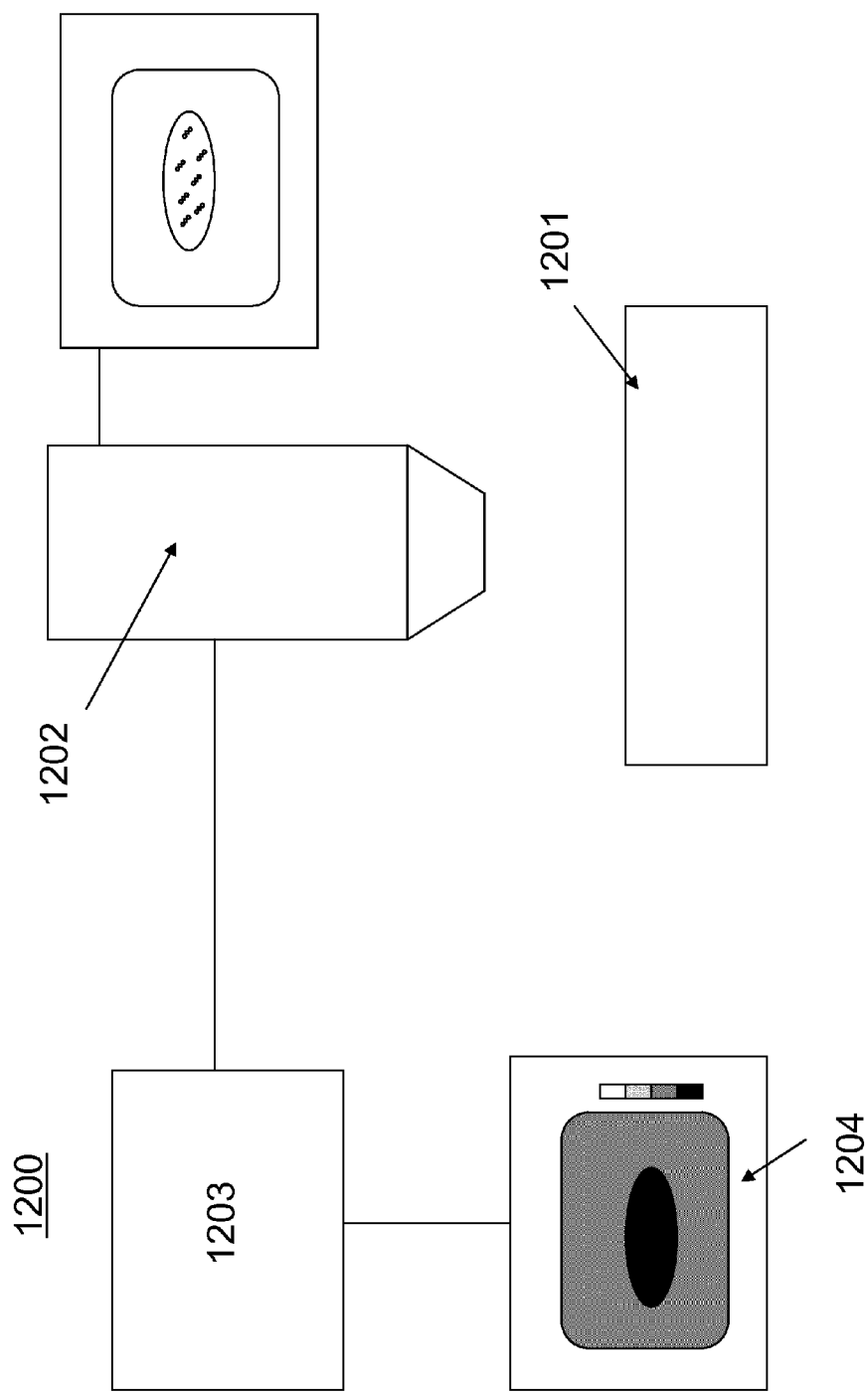
FIG. 12 is a schematic illustrating a detector.

FIG. 12 shows a detector 1200 for detecting a condition (e.g., temperature) of an environment 1201 (e.g., a test tube, a microscope slide, a container, an in vivo environment, or any other suitable environment). A resonant material 100 of the type described herein is introduced into the environment, e.g., in the form of a colloidal suspension, as a powdered solid materials adhered on a suitable substrate, or any other suitable form.

A detector 1202 detects a property of the plasmon resonance of the material while the material is in the environment or in contact with the environment. In one embodiment, detector 1202 is a microscope equipped with a spectrometer and a digital image detector (e.g., a CCD). Detector 1202 may acquire absorbance (or reflectance or emittance) spectra for the resonant material located at one or more locations in the environment 1201. In various embodiments, any suitable detector known in the art may be used, including a photodetector, a photographic recording medium, a digital camera, various diffractive, refractive, or reflective elements, etc. Detector 1202 may include a display (e.g., an electronic display, an eyepiece, a projector, a printer, etc.) which allows a user to view the environment 1201 under detection.

The detector 1202 is coupled to a processor 1203 (e.g., including, a general purpose computer, a microprocessor, a memory device, etc.). Processor 1203 receives information about the detected property of the resonance from detector 1202, and processes the information to determine information indicative of a condition of the environment. In some embodiments, processor 1203 may control one or more functions of the detector 1202.

In one embodiment, the processor 1203 receives absorbance spectra of the resonant material 100 (not shown) at locations in the environment 1201 for the detector. The processor 1203 processes the spectra (e.g., using the techniques described above) to determine a local temperature at the locations within the environment 1201.

An output device 1204 is coupled to processor 1203. The processor 1203 may control the output device 1204 to output information regarding the condition of the environment 1201. The output information may be displayed visually (e.g., using a video monitor, an indicator light, a gauge, a print out, etc.), audibly (e.g., using an alarm buzzer, etc.), or in any other suitable format. In some embodiments, the information may be output in an electronic format, e.g., suitable for storage in a digital medium or transmission to one or more additional devices (not shown). The output unit 1204 may also display other information, e.g., an image of the environment 1201 under observation generated using detector 1202.

In one embodiment, processor 1203 controls output device 1204 to output a false color thermal image of a portion of the environment 1201 under observation, where the false color corresponds to the local temperature at locations in the environment.

Figure 13:
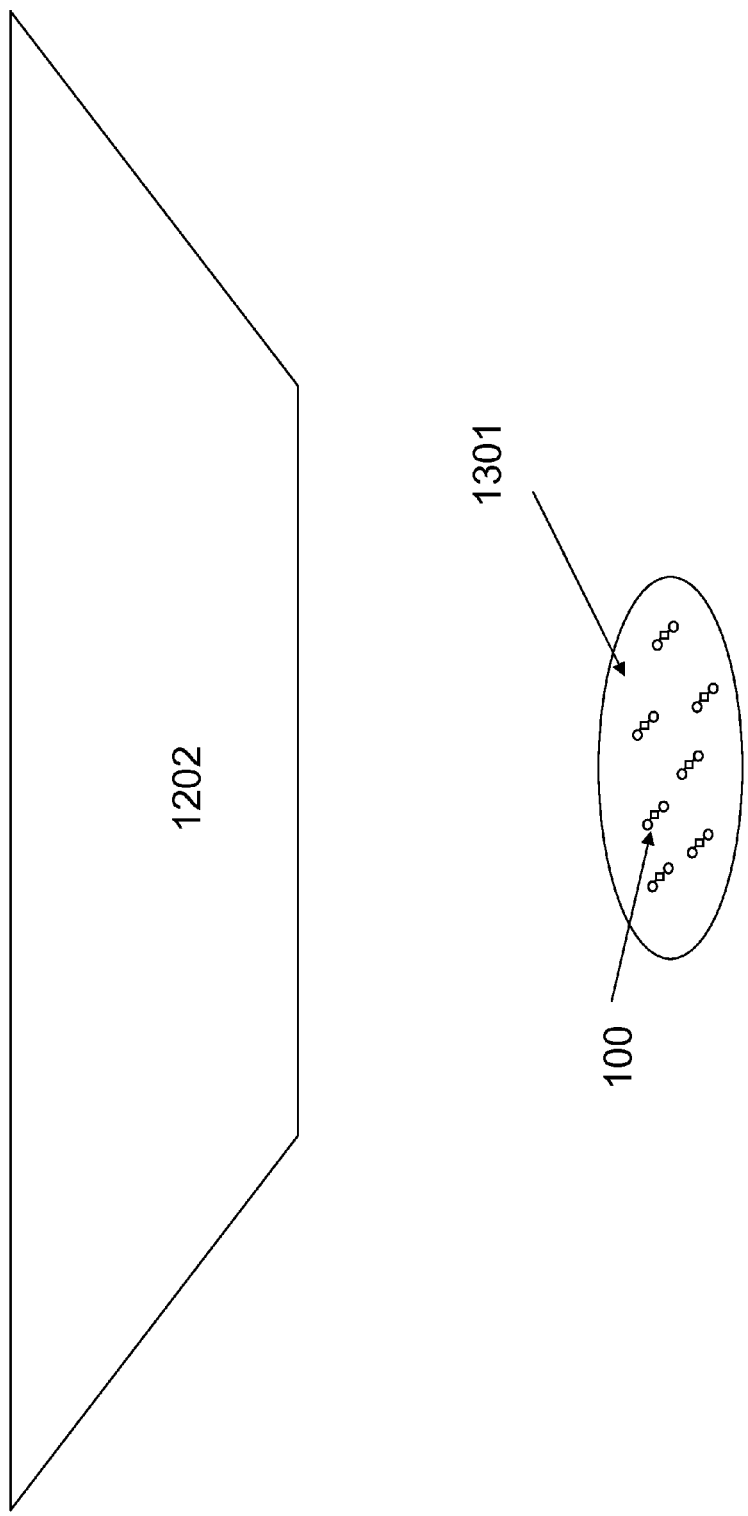
FIG. 13 is a schematic illustrating a detector for detecting intracellular temperature.

FIG. 13 illustrates the use of detector 1200 for the detection of the intracellular temperature of a microorganism 1301. Resonant material 100 is introduced (e.g., as a colloidal suspension) into the intracellular environment of the microorganism. Detector 1202 detects the absorbance spectra of the resonant material 100 at locations within the cell. The spectra are processed by processor 1203 (not shown), to determine the temperature at locations within the cell. The temperature information is output to output device 1204 as a false color thermal image of the cell.

In some embodiments, this detection technique may provide advantageous information about the inner workings of the microorganism 1301. For example, in one embodiment, the microorganism 1301 is a thermophillic bacteria (a bacteria growing at high temperature, e.g., between 40° C. and 105° C., between 45° C. and 80° C., between 80° C. and 100° C.). Examples of thermophillic species are *Thermus aquaticus* and *Thermococcus litoralis*. Using the detector 1200, the cytoplasmic temperature of the bacteria may be determined. This information may be used to determine if the bacteria is made up of thermally resistant biomolecules (suggested if the internal temperature is substantially the same as the media temperature), or includes some type of internal cooling mechanism (suggested if the internal temperature is lower than the temperature of the media).

As will be understood by those skilled in the art, the above described sensing techniques may be applied to a wide variety of applications. In some embodiments, sensing probes may be used in assessing thermal conditions (and metabolic activities) of engineered tissues. In order to study the effect of temperature on the metabolic activity of an engineered tissue one may first want to know the temperature within a cell of the tissue. Sensing materials and techniques as described herein may provide information about the temperature distribution within the tissue without major perturbation to its metabolic activity.

Although several embodiments of temperature sensors have been described, it is to be understood that other environmental conditions may be detected using the materials, devices and techniques described herein.

EXAMPLE

Tryptophan-Based EIDPR Material

In the following example a tryptophan molecule serves as a template molecule for use with silver nanoparticles to form a resonant material having a nanoscale sandwich structure which produces EIDPR response.

Figure 2A:
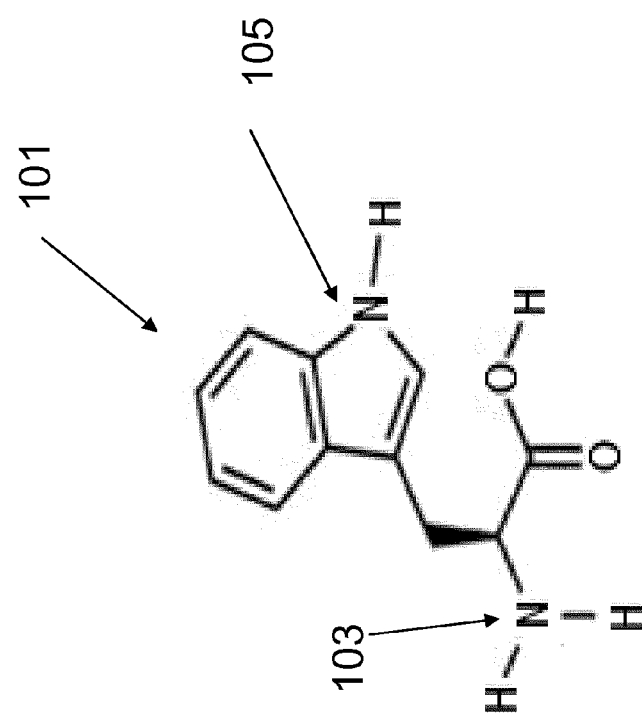
FIG. 2A is an illustration of a template molecule.

As illustrated in FIG. 2A, is a tryptophan molecule is used as template molecule 101. The tryptophan molecule includes two nitrogen centers 103 and 105 which exhibit an affinity for silver nanoparticles. Using methods described below, clusters 102 and 104 of silver nanoparticles (SNP) are formed at the nitrogen centers, resulting in the resonant material 100 shown in FIG. 2B. Note that the clusters 102 and 104 are formed spaced apart from each other by multiple carbon bonds of the tryptophan molecule, resulting in the sandwich structure described above.

FIG. 3 shows atomic force (AFM) microscope images which illustrates the sandwich structured resonant material 100 using tryptophan as a template molecule to which silver nanoparticles (SNP) have conjugated. The images were obtained using an Veeco multi mode NanoScope IIIa AFM using a tapping mode with a tip model RTESPA equipped with 1-10 ohm-cm phosphorous (n)-doped Si at a scanning rate of 1 Hz utilizing a phase data type and a resonant frequency of 314.5 kHz. The sample was prepared by allowing a drop of the nanoparticle suspension to fail on a thin sheet of mica and air dry for further measurement of the sample by AFM.

Referring still to FIG. 3, the upper left panel shows SNP conjugated to the D-stereoisomer of tryptophan, the upper right panel shows SNP conjugated to the L-stereoisomer of tryptophan. The lower panel shows unconjugated SNP. In each panel of the figure the length scale is 1 micron. Note that the tryptophan conjugated SNP exhibit an asymmetric morphology, corresponding to the sandwich structure described above. In contrast, the unconjugated SNP clusters are roughly symmetric, indicating a lack of sandwich structure.

FIG. 4A shows a plot of absorbance as a function of wavelength for a resonant material 100 featuring tryptophan conjugated SNP. The plot includes two peaks, corresponding to a pair of resonant wavelengths $\lambda_1$ and $\lambda_2$, referred to as a double resonance (DR). The strength the resonant peaks are similar, so the resonance may be referred to as an EIDPR. This double resonant behavior corresponds to a surface plasmon resonance of the clusters 102 and 104 of silver nanoparticles in the sandwich configuration as shown in FIG. 2B The double resonance behavior of the tryptophan based resonant material differs significantly from the resonant behavior exhibited by bare clusters silver nanoparticles (i.e., material lacking the sandwich structure). FIG. 4B shows a plot of absorbance as a function of wavelength for bare SNP clusters. Note that the plot includes only a single resonant peak, and lacks the EIDPR structure.

Similarly, FIG. 4C shows a comparison of plots of absorbance versus wavelength for SNP conjugated to the D-stereoisomer of tryptophan, SNP conjugated to the L-stereoisomer of tryptophan, and unconjugated SNP. Both forms of tryptophan templated structures exhibit the EIDPR, while the unconjugated SNP exhibits only a single resonant peak.

FIGS. 5A and 5B show plots of the dependence of the resonant wavelengths $\lambda_1$ and $\lambda_2$ as a function of temperature for a resonant material 100 featuring tryptophan conjugated SNP which exhibits an EIDPR (as shown in FIG. 4A). Note that $\lambda_1$ varies most strongly with temperature in the range of 55-60° C., while $\lambda_2$ varies most strongly with temperature in the range of 70-80° C. FIG. 5C shows a plot of absorbance at each peak wavelength ($\lambda_1$ and $\lambda_2$) as a function of temperature for the same material. Note that the rate change in absorbance as a function of temperature differs for the two peaks, with the peak at $\lambda_2$ exhibiting a more rapid extinction as the temperature is increased from 0-100° C. This temperature dependence makes that material suitable for use in various embodiments of the sensing and detection devices and techniques described above FIG. 7 illustrates a method used to produce the tryptophan resonant material descried in this Example. Silver nanoparticles are be synthesized by first cooling the solution of tryptophan (template molecule 101) and Ag+ (from silver nitrate $AgNO_3$), to a temperature of 4° C. and then adding sodium borohydride ($NaBH_4$) as a reducing agent, e.g., in a ratio of 1:80 ($AgNO_3$: $NaBH_4$) followed by vigorous and uniformly shaking of the reaction mixture. A reddish purple color (unlike the pale yellow color of bare silver nanoparticle) appears after the addition of $NaBH_4$ and the color may stabilize within 3 hours of reaction. The foregoing reactions are conducted in milli Q grade water.

Figure 7:
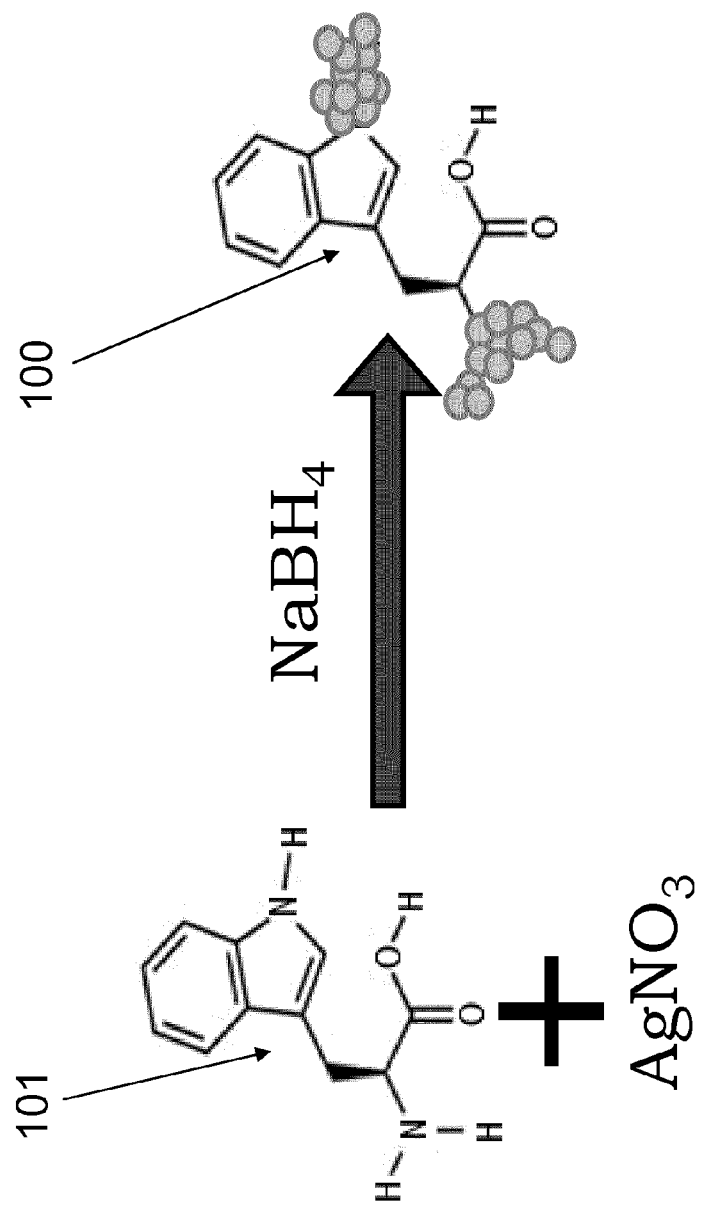
FIG. 7 is an illustration of a method of making a resonance material.

As shown in FIG. 7, it is believed the silver nanoparticles have strong affinity towards the nitrogen of the tryptophan molecules, the clustering of nanoparticles firstly occurs at the two nitrogen centre of tryptophan and these two clusters are spaced by the carbon-carbon bonds of the tryptophan molecule.

There are two possible sites (nitrogen centers) in a tryptophan molecule where the affinity of silver ion is high and the possible site of attraction of silver ion to the tryptophan amino acids are the two nitrogen atoms which are rich in electron and can attract the silver ion of silver nitrate ($AgNO_3$). As both nitrogen centers of tryptophan have almost equal affinity to the silver ion, reducing with borohydride results in bi-directional growth of two separate clusters of nanoparticle spaced apart by a carbon-carbon bond. This results in a sandwich structure in the nanoscale. This kind of sandwich structure is not seen when a similar templating technique is applied to amino acids cases, like glutamine, arginine or cysteine as, in all such cases either there are more than two potent sites of silver ion attachment, or among two such sites (as in case of cysteine) one has unmatched affinity relative to the other (e.g., a sulfur and a nitrogen site). Similarly in case of glutamine, there exist three different potent sites (two nitrogen and one oxygen containing group) precluding the formation of a sandwich structure. Morphologically these molecules, when used as a template, tend to produce nanoparticle structures which mimic the unbonded silver nanoparticle.

Figure 14:
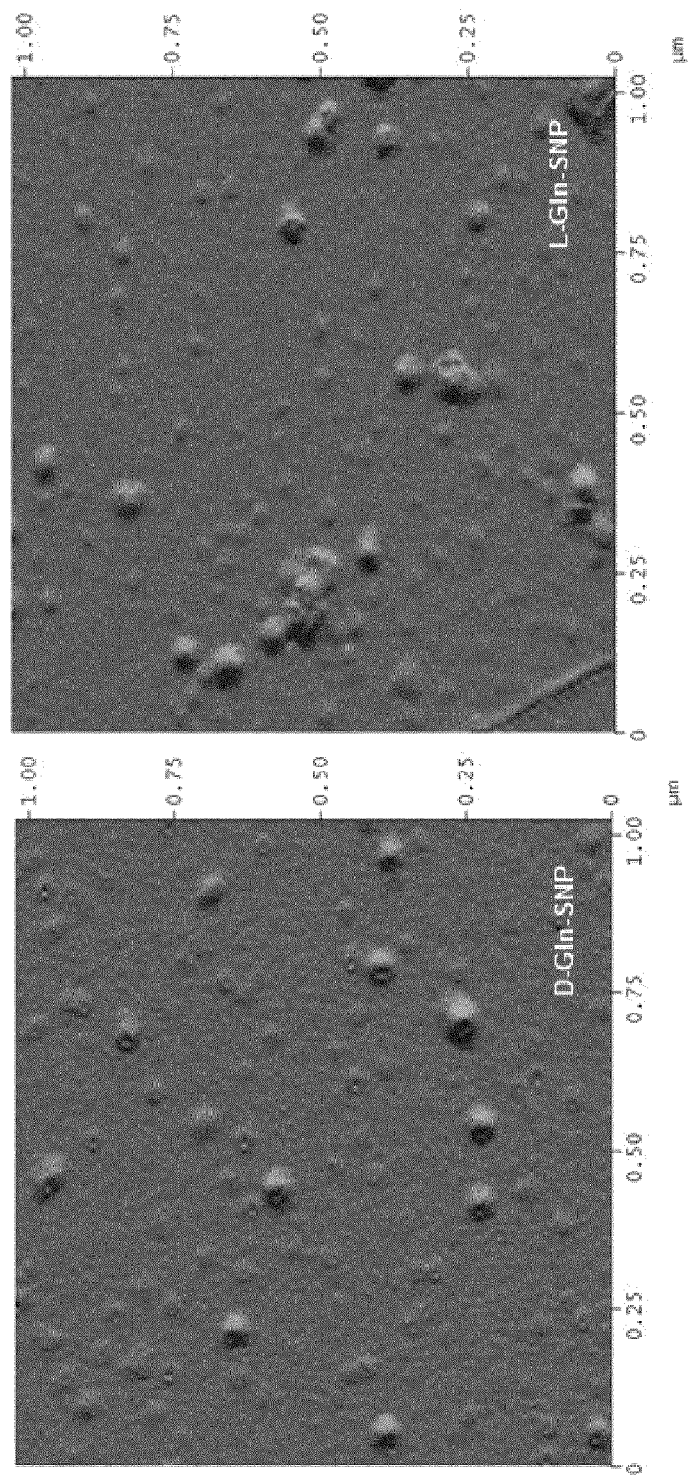
FIG. 14 shows AFM images of silver nanoparticles conjugated with glutamine (left pane shows the D-stereoisomer, the right pane shows the L-stereoisomer)

For example, FIG. 14 shows AFM images of silver nanoparticles conjugated with glutamine (left pane shows the D-stereoisomer, the right pane shows the L-stereoisomer) which have similar morphology to bare silver nanoparticles (e.g., as shown in FIG. 4, bottom panel).

Figure 15:
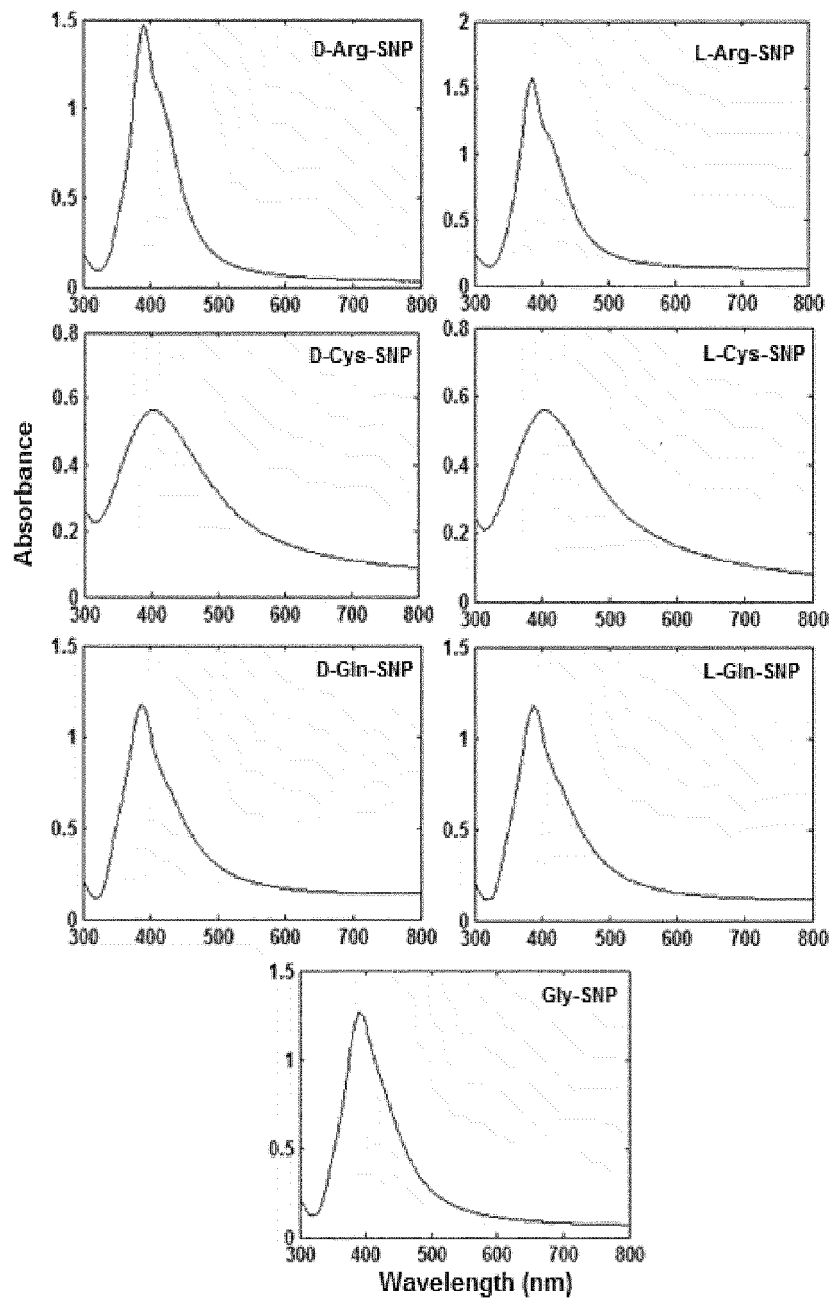
FIG. 15 shows a series of plots illustrating the single resonance of resonant materials formed using glycine, glutamine, arginine or cysteine as a template molecule.

As shown in FIG. 15, glycine, glutamine, arginine or cysteine, when used as a template molecule to form a resonant material using the techniques described herein where the nanoclusters are formed simultaneously, do not exhibit a double resonance. As will be apparent to one skilled in the art, this behavior can be used to detect the presence (or absence) of tryptophan in a substance to be analyzed.

Although, in the particular example above, glycine, glutamine, arginine or cysteine templates did not produce EIDPR structures, it should be understood that this may not be the case for all templating techniques. For example, a double resonant material may be prepared by forming the spaced apart nanoparticle clusters serially instead of only simultaneously. For example, it may be made by blocking/protecting one nitrogen, building the first cluster, deblocking/unprotecting, then building the second cluster.

For example, in an arginine template molecule, there are four nitrogen centers. In techniques where the bare arginine template molecule is exposed to metallic ions to form nanoclusters, the four centers may all attract metallic ions, and serve to frustrate the formation of a nanocluster sandwich structure of the type described above. For example, this effect may be one explanatory factor for the lack of EIDPR behavior in arginine templated silver nanoparticles formed using certain methods, as describe above. However, using alternative techniques, one can generate a sandwich structure using a arginine template molecule. In some embodiments, one selectively blocks two of the four centers. The template molecule is then exposed to metallic ions (e.g., silver ions)

thereby generating a nanoparticle cluster at each of the two unblocked nitrogen centers on the molecule. The resulting structure will have two nanoparticle clusters spaced apart, providing a sandwich structure that may give rise to an EIDPR effect.

In another example, in a tyrosine template molecule, there is amine ($-NH_2$) functional group and a hydroxyl ($-OH$) functional group. These two functional groups have unmatched affinity towards metallic ions, e.g., silver ions. In techniques where the bare tyrosine template molecule is exposed to metallic ions to form nanoclusters, this unmatched affinity may frustrate the formation of a sandwich structure having two nanoclusters (e.g., of similar size) spaced apart by a distance. This difficulty may be overcome by selectively blocking the functional groups. First, the amine group is blocked while the hydroxyl group is exposed to metallic (e.g., silver) ions to form a first nanocluster at the site of the hydroxyl group. The amine group is then unblocked and exposed to metallic ions, generating the nanocluster at this site. Accordingly, the resulting structure will have two nanoparticle clusters spaced apart, providing a sandwich structure that may give rise to an EIDPR effect.

Although two examples have been provided above, as will be understood by those skilled in the art, these techniques may be applied to a variety of possible template molecules. Affinity sites or functional groups may be selectively blocked using any suitable technique know in the art, e.g., those described in Greg T. Hermason, *Bioconjugate Techniques*, Elsevier (2008).

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis, preprocessing, and other methods described herein can also be implemented as a computer-readable storage medium, configured with a computer program, where the storage medium so configured causes a computer to operate in a specific and predefined manner to perform the functions described herein. In some embodiments, the computer readable media is tangible and substantially non-transitory in nature, e.g., such that the recorded information is recorded in a form other than solely as a propagating signal.

Figure 16:
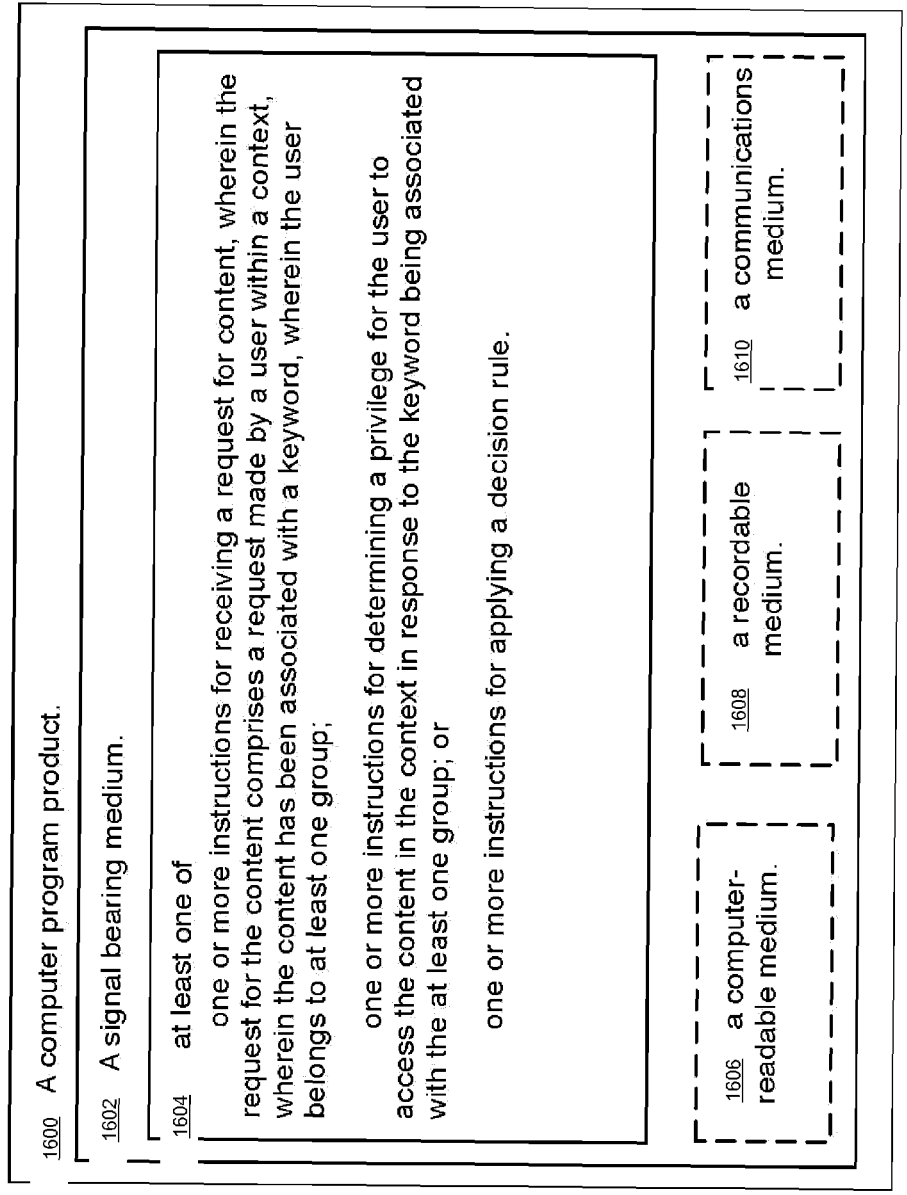
FIG. 16 is a schematic diagram illustrating an example computer program product that includes a computer program for executing a computer process on a computing device; all arranged according to at least some embodiments presented herein.

FIG. 16 illustrates an example computer program product 300 arranged in accordance with at least some examples of the present disclosure. Program product 1600 may include a signal bearing medium 1602. Signal bearing medium 1602 may include one or more instructions 1604 that, when executed by, for example, a processor, may provide the functionality described above with respect to FIG. 8 and FIG. 12. Thus, for example, processor 1203 may undertake one or more of the processes shown in FIG. 8 in response to instructions 1604 conveyed to the processor 1203 by medium 1602.

In some implementations, signal bearing medium 1602 may encompass a computer-readable medium 1606, such as, but not limited to, a hard disk drive, a Compact Disc (CD), a Digital Video Disk (DVD), a digital tape, memory, etc. In some implementations, signal bearing medium 1602 may encompass a recordable medium 1608, such as, but not limited to, memory, read/write (R/W) CDs, R/W DVDs, etc. In some implementations, signal bearing medium 302 may encompass a communications medium 1610, such as, but not limited to, a digital and/or an analog communication medium (e.g., a fiber optic cable, a waveguide, a wired communications link, a wireless communication link, etc.). Thus, for example, program product 1600 may be conveyed to the detector 1200 (e.g., to the processor 1203) by an RF signal bearing medium 1602, where the signal bearing medium 1602 is conveyed by a wireless communications medium 1610 (e.g., a wireless communications medium conforming to the IEEE 802.11 standard).

As used herein the term "light" and related terms (e.g. "optical") are to be understood to include electromagnetic radiation both within and outside of the visible spectrum, including, for example, ultraviolet and infrared radiation.

It is to be understood that any of the signals and signal processing techniques may be digital or analog in nature, or combinations thereof.

In various embodiments, resonant material 100 may exhibit one or more absorbance, reflectance, or emittance peaks. The peaks may be located in the UV (10-400 nm), visible (380-760 nm), near infrared (750-2500 nm), infrared (750-1 mm), microwave (1-1000 mm), or other suitable portion of the electromagnetic spectrum The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of detecting a temperature of an environment, the method comprising:
   introducing a material to the environment, the material comprising:
     a template molecule;
       wherein the template molecule is tryptophan, tryptophan alkyl ester, or methionine;
     a first cluster of two or more silver nanoparticles located at a first affinity site on the template molecule, wherein the first affinity site includes at least one of: a nitrogen atom or a sulfur atom; and
     a second cluster of two or more silver nanoparticles located at a second affinity site on the template molecule and spaced apart from the first cluster, wherein the second affinity site includes at least one of: a nitrogen atom or a sulfur atom;
     wherein the template molecule, the first cluster of two or more silver nanoparticles, and second cluster of two or more silver nanoparticles form a molecular sandwich structure;
   irradiating the material so as to cause the first cluster of silver nanoparticles to exhibit a plasmon resonance having a first resonant peak, and the second cluster of silver nanoparticles to exhibit a plasmon resonance having a second resonant peak;
     wherein the first resonance peak has a first absorbance value, the second resonance peak has a second absorbance value, and the first and second absorbance values differ by less than 25%;
   detecting at least one characteristic of the plasmon resonance of the material; and
   determining information indicative of the temperature of the environment based on the at least one detected characteristic of the plasmon resonance of the material;
   wherein the temperature is from about 0° C. to about 100° C.

2. The method of claim 1, wherein the at least one characteristic of the plasmon resonance of the material is selected from the group consisting of: a wavelength of the first resonant peak; a wavelength of the second resonant peak; an extinction coefficient associated with the first resonant peak; and an extinction coefficient associated with the second resonant peak.

3. The method of claim 1, wherein the at least one characteristic of the plasmon resonance of the material comprises at least two different characteristics selected from the list consisting of: a wavelength of the first resonant peak; a wavelength of the second resonant peak; an extinction coefficient associated with the first resonant peak; and an extinction coefficient associated with the second resonant peak.

4. The method of claim 1, wherein the at least one characteristic of the plasmon resonance of the material comprises at least three different characteristics selected from the list consisting of: a wavelength of the first resonant peak; a wavelength of the second resonant peak; an extinction coefficient associated with the first resonant peak; and an extinction coefficient associated with the second resonant peak.

5. The method of claim 1, wherein the at least one characteristic of the plasmon resonance of the material comprises a wavelength of the first resonant peak; a wavelength of the second resonant peak; an extinction coefficient associated with the first resonant peak; and an extinction coefficient associated with the second resonant peak.

6. The method of claim 1, wherein detecting at least one characteristic of the plasmon resonance of the material comprises detecting an absorbance spectrum of the material.

7. The method of claim 1, wherein the silver nanoparticles are spherical.

* * * * *

UNITED STATES PATENT AND TRADEMARK OFFICE
CERTIFICATE OF CORRECTION

| | | |
|---|---|---|
| PATENT NO. | : 9,068,939 B2 | Page 1 of 1 |
| APPLICATION NO. | : 13/503815 | |
| DATED | : June 30, 2015 | |
| INVENTOR(S) | : Dasgupta et al. | |

It is certified that error appears in the above-identified patent and that said Letters Patent is hereby corrected as shown below:

In the specification

Column 1, Lines 8-11, delete "The present application claims priority to a corresponding patent application filed in India and having application number 375/KOL/2011, filed on Mar. 21, 2011, the entire contents of which are herein incorporated by reference." and insert -- The present application is a national stage entry under 35 § U.S.C. 371(c) of International Application No: PCT/IB2011/001392, entitled Nano Sensing Using Plasmon Resonance, filed on June 21, 2011, which in turn claims priority to a corresponding patent application filed in India and having application number 375/KOL/2011, filed on March 21, 2011, the entire contents of each of which are herein incorporated by reference. --, therefor.

Column 2, Line 6, delete "wavelength the" and insert -- wavelength of the --, therefor.

Column 6, Line 63, delete "peak" and insert -- peak. --, therefor.

Column 13, Line 13, delete "fail" and insert -- fall --, therefor.

Column 13, Line 33, delete "FIG. 2B" and insert -- FIG. 2B. --, therefor.

Column 13, Line 61, delete "above" and insert -- above. --, therefor.

Column 14, Line 64, delete "using a" and insert -- using an --, therefor.

Column 16, Line 35, delete "spectrum" and insert -- spectrum. --, therefor.

Signed and Sealed this
First Day of December, 2015

Michelle K. Lee
*Director of the United States Patent and Trademark Office*